(12) United States Patent
Zhang et al.

(10) Patent No.: US 10,309,907 B2
(45) Date of Patent: Jun. 4, 2019

(54) ALL REFLECTIVE WAFER DEFECT INSPECTION AND REVIEW SYSTEMS AND METHODS

(71) Applicant: KLA-Tencor Corporation, Milpitas, CA (US)

(72) Inventors: Shiyu Zhang, Fremont, CA (US); Wei Zhao, Saratoga, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 117 days.

(21) Appl. No.: 15/055,292

(22) Filed: Feb. 26, 2016

(65) Prior Publication Data

US 2016/0258878 A1    Sep. 8, 2016

Related U.S. Application Data

(60) Provisional application No. 62/128,465, filed on Mar. 4, 2015, provisional application No. 62/127,827, filed
(Continued)

(51) Int. Cl.
*G01N 21/88* (2006.01)
*G01N 21/95* (2006.01)
(Continued)

(52) U.S. Cl.
CPC ..... *G01N 21/8806* (2013.01); *G01N 21/9501* (2013.01); *G02B 13/143* (2013.01);
(Continued)

(58) Field of Classification Search
CPC .................................................. G01N 21/8806
(Continued)

(56) References Cited

U.S. PATENT DOCUMENTS 5,294,990 A * 3/1994 Aoki .................... H04N 5/2253
348/230.1
5,796,524 A * 8/1998 Oomura ............. G02B 17/0804
359/633
(Continued)

FOREIGN PATENT DOCUMENTS

FR          2617985 A1    1/1989
JP       2009204608 A    9/2009
(Continued)

OTHER PUBLICATIONS

"International Application Serial No. PCT/US2016/021036, Search Report dated May 30, 2016", 6 pgs.
(Continued)

*Primary Examiner* — Tarifur R Chowdhury
*Assistant Examiner* — Omar Nixon
(74) *Attorney, Agent, or Firm* — Kwan & Olynick LLP

(57) ABSTRACT

Disclosed are methods and apparatus for reflecting, towards a sensor, an Infrared to vacuum ultra-violet (VUV) light that is reflected from a target substrate. The system includes a first mirror arranged to receive and reflect the Infrared to VUV light that is reflected from the target substrate and a second mirror arranged to receive and reflect Infrared to VUV light that is reflected by the first mirror. The first and second mirrors are arranged and shaped so as to reflect Infrared to VUV light from the target substrate towards an optical axis of the apparatus. In another embodiment, the apparatus can also include a third mirror arranged to receive and reflect the Infrared to VUV light that is reflected by the second mirror and a fourth mirror arranged to receive and reflect such illuminating light that is reflected by the third mirror towards the sensor. In one more embodiment, a reflecting or refracting optics is used to relay the image by above optics to the sensor; various magnification is achieved by adjusting the distance between the intermediate image and the relay optics.

22 Claims, 12 Drawing Sheets

Related U.S. Application Data on Mar. 4, 2015, provisional application No. 62/163,979, filed on May 20, 2015.

(51) Int. Cl.
| | | |
|---|---|---|
| *G03F 7/20* | (2006.01) | |
| *G03F 1/84* | (2012.01) | |
| *G02B 13/14* | (2006.01) | |
| *G02B 17/06* | (2006.01) | |
| *G01N 21/956* | (2006.01) | |

(52) U.S. Cl.
CPC .......... *G02B 17/0652* (2013.01); *G03F 1/84* (2013.01); *G03F 7/7065* (2013.01); *G01N 21/956* (2013.01); *G01N 2021/8845* (2013.01)

(58) Field of Classification Search
USPC ..................................................... 356/237.5
See application file for complete search history.

(56) References Cited

U.S. PATENT DOCUMENTS

| | | | |
|---|---|---|---|
| 6,333,811 B1 * | 12/2001 | Tatian .................... | G02B 15/14 359/365 |
| 6,894,834 B2 | 5/2005 | Mann et al. | |
| 6,907,390 B1 * | 6/2005 | Reffner .............. | G02B 21/0008 359/380 |
| 2001/0043391 A1 * | 11/2001 | Shafer .................... | G02B 13/22 359/365 |
| 2004/0114217 A1 | 6/2004 | Mann et al. | |
| 2004/0246595 A1 * | 12/2004 | Beach ................ | G02B 17/0804 359/728 |
| 2005/0111081 A1 | 5/2005 | Shafer et al. | |
| 2005/0280906 A1 | 12/2005 | Scheiner et al. | |
| 2009/0185153 A1 * | 7/2009 | Epple .................. | G03F 7/70225 355/67 |
| 2009/0202138 A1 | 8/2009 | Ito et al. | |
| 2010/0033716 A1 | 2/2010 | Tsai et al. | |
| 2010/0149662 A1 | 6/2010 | Armstrong | |
| 2010/0188738 A1 | 7/2010 | Epple et al. | |
| 2011/0032481 A1 * | 2/2011 | Uchida .................. | A61B 3/152 351/208 |
| 2011/0242528 A1 * | 10/2011 | Hwang .............. | G01N 21/9501 356/237.2 |
| 2012/0236277 A1 * | 9/2012 | Schicketanz ........... | G02B 13/14 355/53 |
| 2013/0038719 A1 * | 2/2013 | Canini ............... | G06K 7/10732 348/135 |
| 2013/0063716 A1 * | 3/2013 | Mann ................... | G02B 5/0891 356/51 |
| 2013/0070221 A1 * | 3/2013 | Bittner ................. | G03F 7/7005 355/30 |
| 2013/0265572 A1 | 10/2013 | Delgado | |
| 2014/0118819 A1 | 5/2014 | Sanson | |
| 2014/0211183 A1 * | 7/2014 | Omura ................ | G03F 7/70225 355/67 |
| 2014/0218704 A1 * | 8/2014 | Williamson ....... | G02B 17/0657 355/67 |
| 2014/0375981 A1 * | 12/2014 | Wang .................. | G01N 21/9501 356/51 |

FOREIGN PATENT DOCUMENTS

| | | |
|---|---|---|
| JP | 2012154902 A | 8/2012 |
| WO | 2009046137 A1 | 4/2009 |

OTHER PUBLICATIONS

EPO International Search Report, Application No. 16759622.0-1022/3213342 PCT/US2016021036. Search dated Apr. 26, 2018.

* cited by examiner

ALL REFLECTIVE WAFER DEFECT INSPECTION AND REVIEW SYSTEMS AND METHODS

CROSS-REFERENCE TO RELATED APPLICATION

This application claims the benefit of prior applications (i) U.S. Provisional Application No. 62/128,465, filed 4 Mar. 2015 by Shiyu Zhang et al., (ii) Provisional Application No. 62/127,827 filed 4 Mar. 2015 by Shiyu Zhang et al, and U.S. Provisional Application No. 62/163,979, filed 20 May 2015 by Shiyu Zhang et al., which applications are herein incorporated by reference in their entirety for all purposes.

TECHNICAL FIELD OF THE INVENTION

The invention generally relates to the field of wafer inspection. More particularly the present invention relates to all reflective systems for inspecting wafers at the spectral band of Infrared down to vacuum UV (VUV) band, or even deeper spectral bands.

BACKGROUND

Generally, the industry of semiconductor manufacturing involves highly complex techniques for fabricating integrating circuits using semiconductor materials which are layered and patterned onto a substrate, such as silicon. An integrated circuit is typically fabricated from a plurality of reticles. Generation of reticles and subsequent optical inspection of such reticles have become standard steps in the production of semiconductors. Initially, circuit designers provide circuit pattern data, which describes a particular integrated circuit (IC) design, to a reticle production system, or reticle writer.

Due to the large scale of circuit integration and the decreasing size of semiconductor devices, the reticles and fabricated devices have become increasingly sensitive to defects. That is, defects which cause faults in the device are becoming increasingly smaller. The device can generally be required to be fault free prior to shipment to the end users or customers.

There is a continuing need for improved inspection systems and, in particular, at a very low wavelength, such as from Infrared down to vacuum ultraviolet (VUV).

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, an apparatus for reflecting, towards a sensor, illuminating light that is reflected from a target substrate is disclosed. The apparatus includes an illumination source for generating infrared to Vacuum UV spectral band light that illuminates a target substrate and objective optics for receiving and reflecting Infrared to Vacuum UV spectral light that is reflected from the target substrate in response to the generated Infrared to Vacuum UV spectral band light that illuminates the target substrate. The apparatus further includes a sensor for detecting Infrared to Vacuum UV spectral light that is reflected by the objective optics, and the objective optics comprises (i) a first mirror arranged to receive and reflect. Infrared to Vacuum UV spectral light that is reflected from the target substrate, (ii) a second mirror arranged to receive and reflect Infrared to Vacuum UV spectral light that is reflected by the first mirror, wherein the first and second mirrors are arranged and shaped so as to reflect Infrared to Vacuum UV spectral light from the target substrate towards an optical axis of the apparatus, (iii) a third mirror arranged to receive and reflect Infrared to Vacuum UV spectral light that is reflected by the second mirror, and (iv) a fourth mirror arranged to receive and reflect Infrared to Vacuum UV spectral light that is reflected by the third mirror towards the sensor.

In a specific implementation, at least one of the first and second mirrors is aspheric so as to reduce a central obscuration on the fourth mirror. In one aspect, the first mirror is spherical and the second, third and fourth mirrors are aspheric. In a further aspect, the first and third mirrors are concave, and the second and fourth mirrors are convex. In another aspect, the first and second mirrors are spherical and the third and fourth mirrors are aspheric; the first, third, and fourth mirrors are concave; and the second mirror is convex. In yet another example, the first, second, third, and fourth mirrors are aspheric; the first, third, and fourth mirrors are concave; and the second mirror is convex. In a specific implementation, a magnification between from the target substrate to an image sensor is between 2× and 1500×. In another aspect, a magnification between from the target substrate to the intermediate image is between 2× and 1500×.

In another implementation, the fourth mirror's size is minimized to limit a back focal distance. In another aspect, the apparatus includes one or more folding mirrors to receive light reflected from the fourth mirror and to relay an intermediate image onto the sensor so as to minimize the footprint of the apparatus. In one example, the one or more folding mirrors comprise a single relay mirror, and the apparatus further comprises a positioning mechanisms for moving the relay mirror so as to vary a distance between an intermediate image and the relay and change a magnification. In another example, the one or more folding mirrors comprise multiple relay mirrors with different focal lengths; and the apparatus further comprises a positioning mechanisms for switching in different ones of the relay mirrors so as to vary a distance between an intermediate image and the relay and change a magnification. In another embodiment; a gap between the second mirror and the fourth mirror has a size into which illumination and/or autofocus is inserted. In another aspect, Infrared to VUV light between the second and third mirrors is near collimated.

In an alternative embodiment, the apparatus includes an illumination source for generating Infrared to VUV light that illuminates a target substrate and objective optics for receiving and reflecting Infrared to VUV light that is reflected from the target substrate in response to the generated Infrared to VUV spectral band light that illuminates the target substrate. This apparatus also includes a sensor for detecting infrared to VUV light that is reflected by the objective optics, and the objective optics comprises (i) a first mirror arranged to receive and reflect infrared to VUV light that is reflected from the target substrate, and (ii) a second mirror arranged to receive and reflect Infrared to VUV light that is reflected by the first mirror towards the sensor. The first and second mirrors are arranged and shaped so as to reflect Infrared to VUV light from the target substrate towards an optical axis of the apparatus.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

Some Infrared to VUV microscope objectives (having multilayer-coated or simple metal coated mirrors), which are designed for defect or pattern review applications with operation in the neighborhood of 13 nm wavelength of light, are based on a four aspheric mirror design. Aspheric surfaces can be difficult and expensive to manufacture and test since they require more process steps than spherical mirrors, which increase manufacturing costs. Additionally, it would be beneficial to design an objective that increases manufacturability for the mirror closest to the wafer and achieves a working distance that is large enough to enable introduction of illumination or autofocus to the target, while minimizing the overall footprint and costs of the inspection tool.

Figure 1:
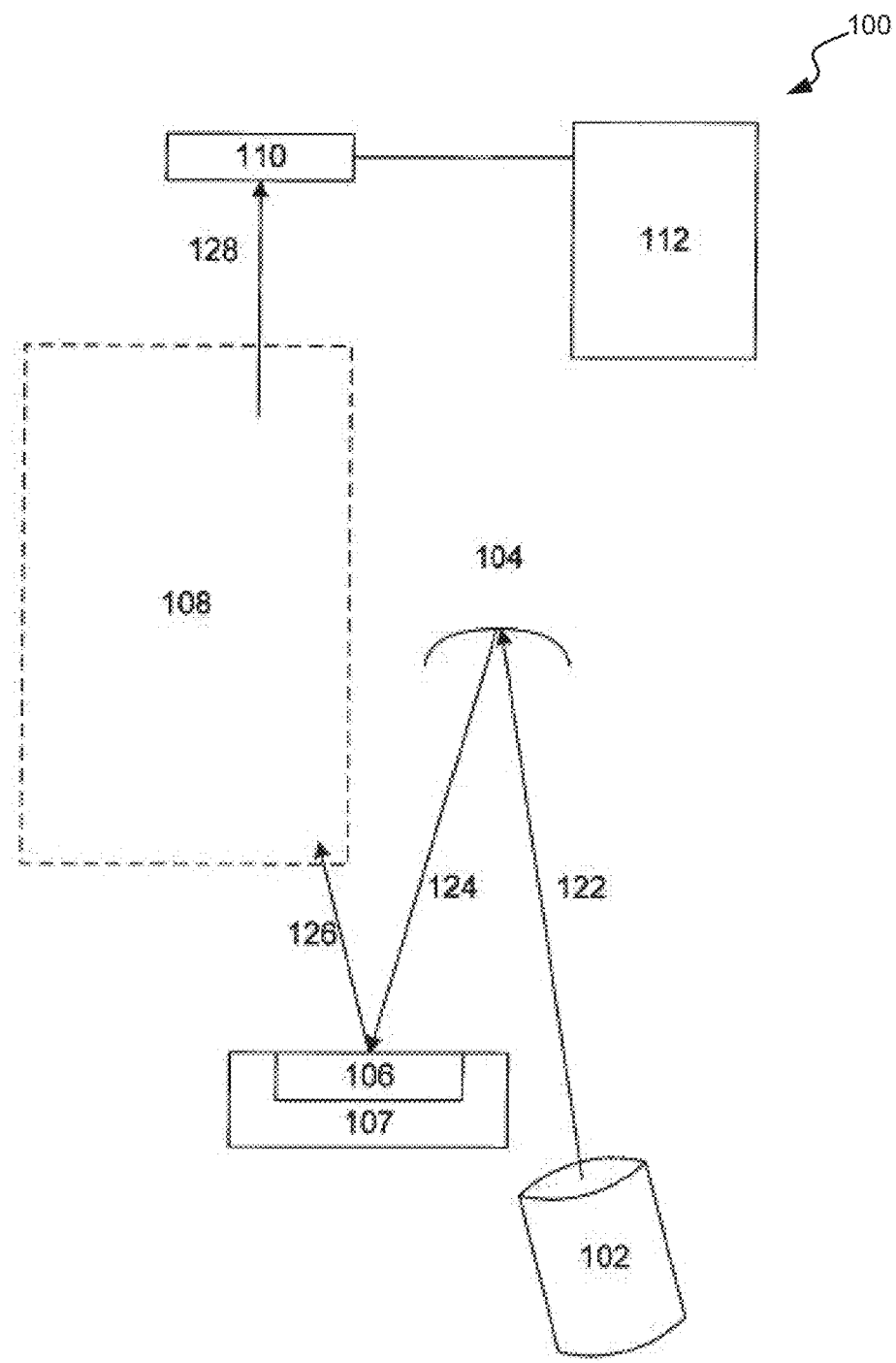
FIG. 1 is a diagrammatic representation of an inspection apparatus in accordance with one embodiment of the present invention.

FIG. 1 is a schematic diagram of an inspection apparatus in accordance with one embodiment of the invention. The apparatus 100 includes an Infrared to VUV illumination source 102, an illumination mirror (or lens system) 104, a target substrate 106, a substrate holder 107, objective optics 108, a sensor (detector) 110, and a data processing system 112.

The illumination source 102 may comprise, for example, a laser-induced plasma source, which outputs a light beam 122. In one embodiment, the light is at a wavelength of about 13.5 nm. The illumination mirror 104 (or lens system) reflects and directs the light such that an incident beam 124 illuminates the target substrate 106. In one embodiment of the invention, the target substrate 106 is a semiconductor wafer that is being inspected. The target substrate 106 may be scanned under the beam 124 by controllably translating the substrate holder 107 so that the field of view (FOV) of the inspection apparatus covers regions on the substrate to be inspected.

Output light 126 is reflected from the target substrate 106 to the reflective objective optics 108. Certain embodiments of the objective optics 108 are described in detail below in relation to FIGS. 2 through 11B.

The objective optics 108 outputs a projection 128 of the output light onto the sensor 110. Suitable sensors include charged coupled devices (CCD), CCD arrays, time delay integration (TDI) sensors, TDI sensor arrays, photomultiplier tubes (PMT), and other sensors.

The signals captured by the sensor 110 can be processed by a data processing system 112 or, more generally, by a signal processing device, which may include an analog-to-digital converter configured to convert analog signals from the sensor 110 into digital signals for processing. The data processing system 112 may be configured to analyze intensity, phase, and/or other characteristics of the sensed light beam. The data processing system 112 may be configured (e.g., with programming instructions) to provide a user interface (e.g., on a computer screen) for displaying resultant test images and other inspection characteristics. The data processing system 112 may also include one or more input devices (e.g., a keyboard, mouse, joystick) for providing user input, such as changing detection threshold. In certain embodiments, the data processing system 112 can also be configured to early out inspection techniques. The data processing system 112 typically has one or more processors coupled to input/output ports, and one or more memories via appropriate buses or other communication mechanisms.

In accordance with one embodiment, the data processing system 112 may process and analyze the detected data for inspection and defect detection. For example, the processing system 112 may be configured to perform the following operations: producing test light intensity images of a sample that include a test transmitted image and/or a test reflected image and analyzing the test light intensity images based on a reference image (from an imaged sample or from a design database) to identify defects.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 2:
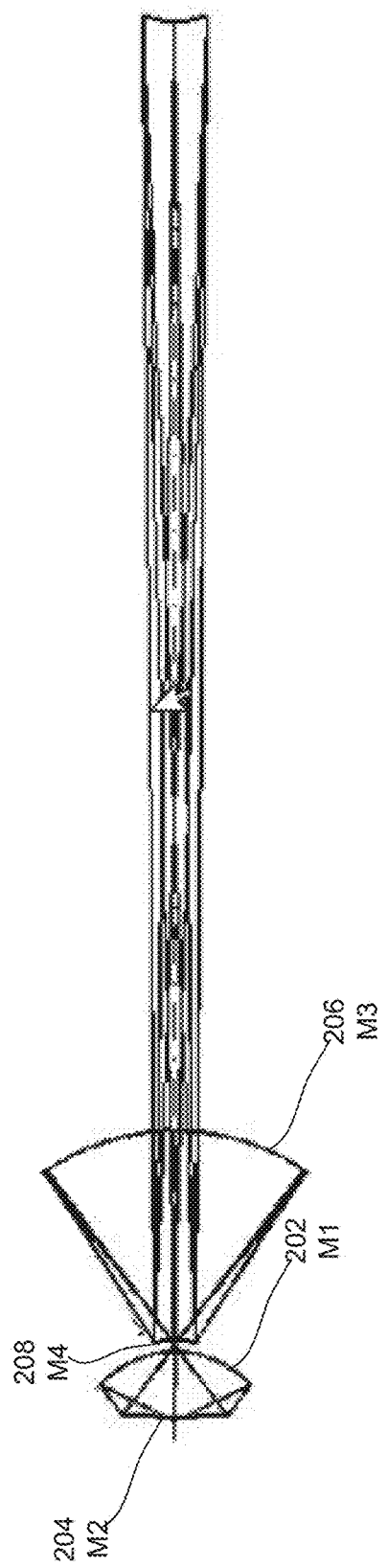
FIG. 2 is an optical ray diagram of a mirror distribution for an example objective optics design form.

FIG. 2 is an optical ray diagram of a mirror distribution for an example objective optics design. In this example, M1, M2, M3, and M4 mirrors (202, 204, 206, and 208) are arranged such that the output light reflects from the M1, M2, M3, and M4 mirrors (202, 204, 206, and 208, respectively) in that order.

Figure 3:
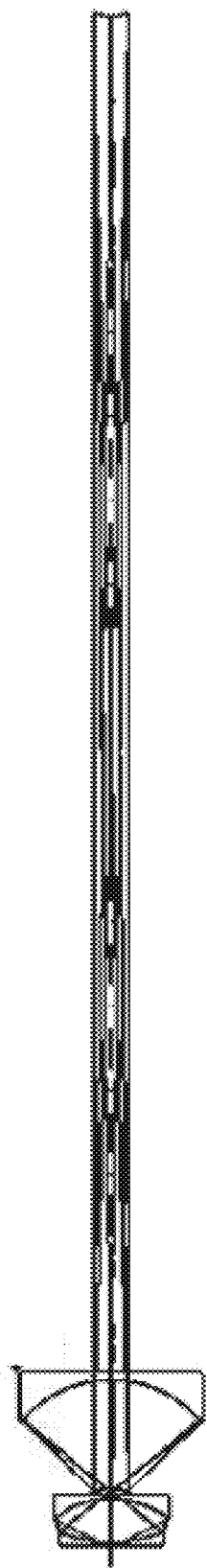
FIG. 3 is an optical ray diagram of a mirror distribution for objective optics having a yet another design form.

FIG. 3 is an optical ray diagram of a mirror distribution for an alternative objective optics design form.

In order to minimize the central obscuration while increasing the manufacturability of the mirror that is the one closest to the wafer plane (e.g., "M2" as indicated in FIG. 2), it is beneficial for M2 to be curved away from the wafer. However, it was a general belief that in order for the mirror M2 to be curved away from the wafer, a curved image will be generated. The curved image generally then requires an image relay to correct for the field curvature, which also increases the number of elements in the system, which reduces the system throughput and increases the cost of ownership of the system.

Figure 4:
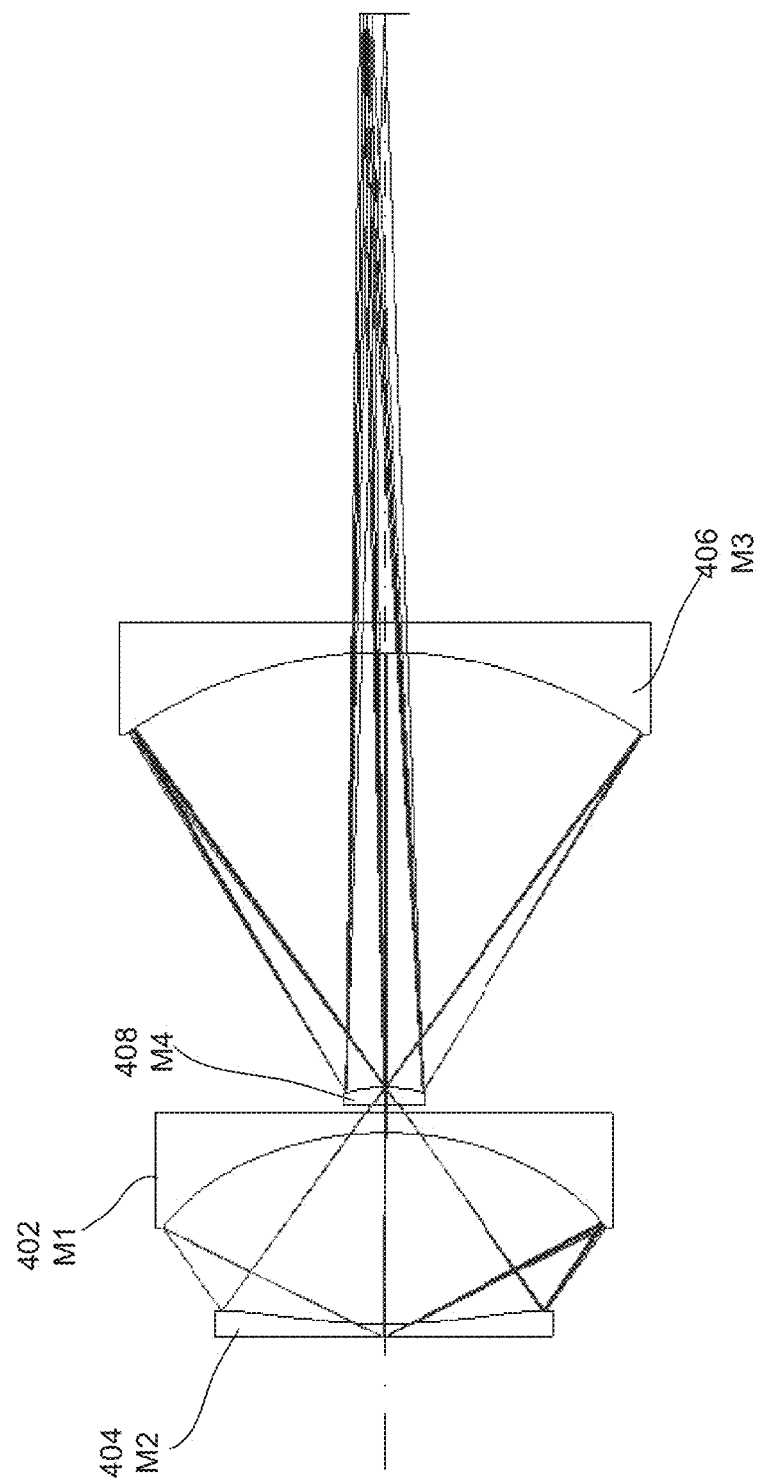
FIG. 4 is an optical ray diagram of an example four mirror distribution for Objective optics.

FIG. 4 is an optical ray diagram of an example four mirror distribution for objective optics. This system utilizes four aspheric mirrors M1, M2, M3, and M4 (402, 404, 406, and 408) to achieve a reasonably good performance over a large field of view. In order to minimize the central obscuration in this design, the mirror which is closest to the wafer plane (M2) needs to be pretty thin, even though this mirror is intentionally shaped to an arch shape to increase substrate thickness. The mirror diameter over the substrate thickness aspect ratio for this mirror M2 also needs to be very high, making the manufacturing very difficult and expensive. In addition, it is difficult to have a working distance that is larger than 1.0 mm for a reasonably sized mirror M2, e.g., 300 mm or so in diameter.

Figure 5:
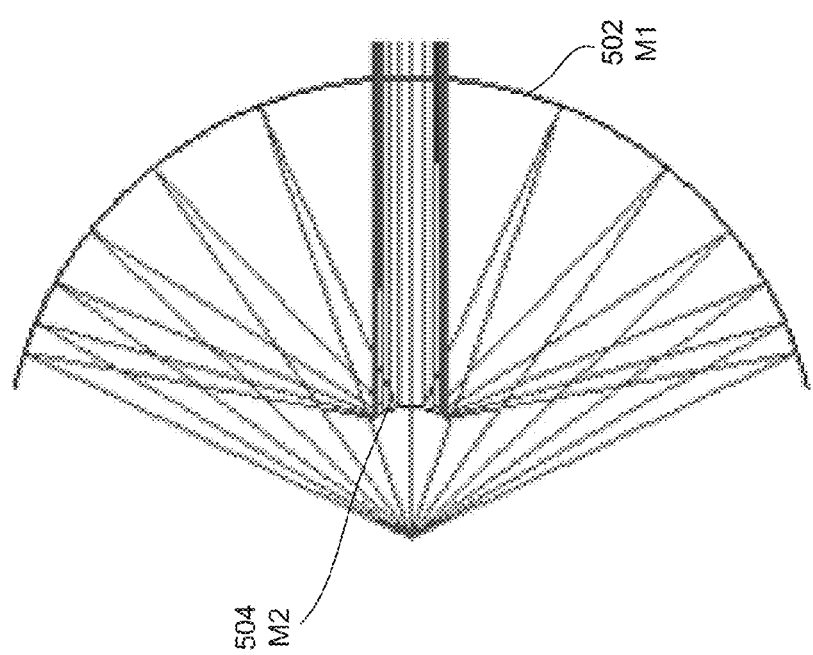
FIG. 5 is an optical ray diagram of another example two mirror distribution for a Schwartzchild objective optics.

In certain other implementations, a very interesting Schwartzchild objective is configured and used as shown in FIG. 5. This objective utilizes a concave aspheric mirror M1 (502) and a convex spherical mirror M2 (504) to achieve a roughly 40 um FOV (field of view) with a Strehl Ratio (S.R.) of 0.82 or more.

This design is counter intuitive because the ray NA goes from large to even larger; while typically for a high NA (numerical aperture) system, it is desirable to gradually reduce the NA of the system. One disadvantage of the Schwartzchild type objective is that the NA increases on the smaller mirror (e.g., M4 408), making the alignment tolerance really tight.

However, this kind of setup has an extremely long working distance, which eliminates the need to manufacture a thin M2 mirror as in FIGS. 2-4. In addition, with the large working distance, the illumination and autofocus can also enter the system through the side of the mirror or beneath M2. It is believed that the benefits out-weight the disadvantage of this design configuration.

It would also be beneficial to replace the M1/M2 objective head, like the one in the four mirror design in FIGS. 2-4, with the Schwartzchild objective.

Figure 6A:
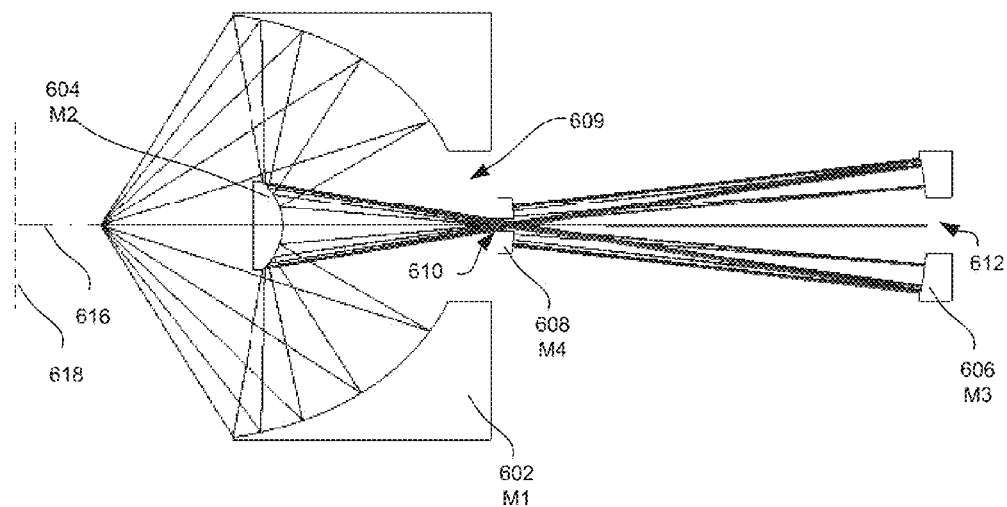
FIGS. 6A and 6B illustrate a 4-mirror design in accordance with a specific first embodiment of the present invention.
Figure 6B:
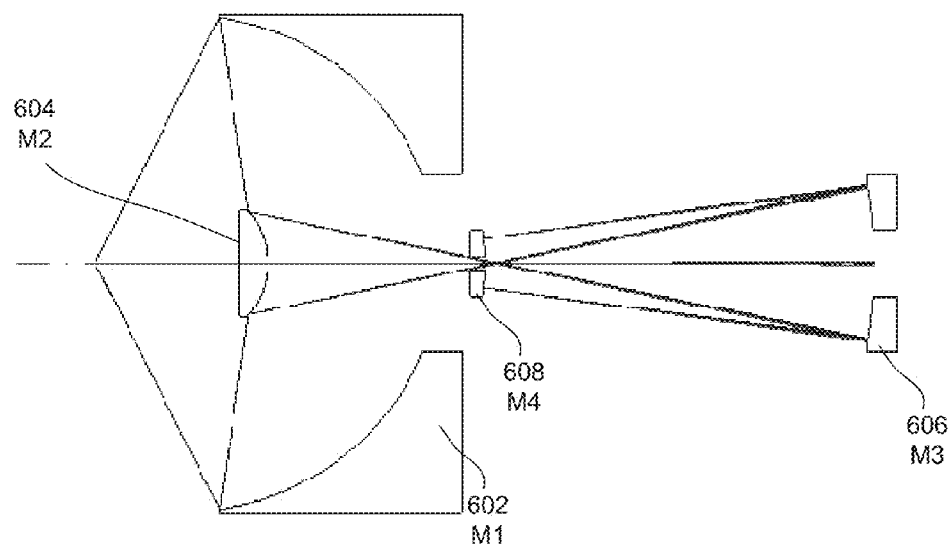

FIGS. 6A and 6B illustrate a 4-mirror design in accordance with a first embodiment of the present invention. FIG. 6A shows a more detailed ray distribution, while FIG. 6B shows a simplified two ray example for illustration purposes only. From the wafer surface, there is a first concave spherical mirror M1 (602), a convex aspherical mirror M2 (604), a concave aspherical mirror M3 (606), and a convex aspherical mirror M4 (608). One feature of this and certain other inventive configurations is that the M1 mirror is arranged to bend rays more towards the optical axis (e.g., 616), than away from target plane 618, which is to say to increase the ray incident angle on mirror M2 (604). Mirror M1 (602) is not necessarily a spherical mirror (it can be aspherized), while mirrors M2 (604), M3 (606) and/or mirror M4 (608) can be spherical mirrors.

An intermediate image is formed between M2 and M3, and roughly at the physical location of the M4. Between M1 and M2, at least one of these two mirrors are constructed as aspheric mirrors in order to reduce the central obscuration on M4. In this particular design example that is shown, M2 and M3 are aspherized, as well as M4.

The size of M4 heavily impacts the overall length (OAL) of the system. The overall length will be roughly:

$$OAL = \frac{Dia_{M4}}{2} * \frac{Mag}{NA},$$

where $Dia_{M4}$ is the diameter of M4, Mag is the magnification of the system, and NA is the numerical aperture at the object.

It is desirable to reduce the size of each mirror, especially the one that is closest to the detector (or TDI), which is M4 in this case, while maintaining a wide or acceptable range of magnification. However, a small aspheric mirror is often difficult to manufacture. Additionally, since a smaller mirror will absorb a lot of heat, thermal management may also be a challenge. In certain embodiments, the M4 mirror has a diameter that is greater than or equal to about 20 mm for a magnification in the range of 2 to 1500×. For this particular design example, the diameter of M4 (Dia_M4) is chosen to be 20 mm, with a system magnification of 600× and a system BA of 0.9 NA. With these specifications, the OAL (over-all length) can be over 10 meters. It is noted that the system is scalable, and the mirrors sizes can be optimized to make them easier to manufacture and test. Effort can also be made to change the magnification by adjusting one or more of the four mirrors axially. For instance, controller 112 may include a positioning mechanism for moving any of the system mirrors of any embodiment.

The lens description for the objective of FIGS. 6A and 6B is listed in Table 1. The field of view (FOV) is about 100 um.

TABLE 1

4-Mirror Embodiment Lens Description

| Element No. | Surface Description | | | Thickness | Glass |
|---|---|---|---|---|---|
| | Radius Value | Shape | Type | | |
| Object | Flat | | | 149.547 | |
| 1 (Stop) | −112.918 | CC | SPH | −74.677 | REFL |
| 2 | −39.520 | CX | ASP | 264.006 | REFL |
| 3 | −196.558 | CC | ASP | −169.232 | REFL |
| 4 | −97.420 | CX | ASP | 7450.505 | REFL |
| IMAGE | Flat | | | | |

The 4-mirror embodiment may also have the following characteristics as illustrated in Table 2:

TABLE 2

4-Mirror Embodiment Characteristics

| | |
|---|---|
| Field size | 100 μm |
| Objective Space NA | 0.9000 |
| Wavelength | 150 nm |

For the tables described herein, it is noted that a positive radius indicates that the center of curvature is to the right of the optical surface, while a negative radius indicates that the center of curvature is to the left (e.g., towards the object). The dimensions are given in millimeters (except where specifically noted), and the thickness is the axial distance to the next surface.

In certain objective system embodiments described herein, at least one of the mirrors is aspherical (i.e., the M2, M3, and M4 mirrors of FIG. 6A). The form of an aspheric surface can be represented by the following Equation_1:

$$z = \frac{cr^2}{1 + \sqrt{1 - (1+k)c^2 r^2}} + Ar^4 + Br^6 + Cr^8 + Dr^{10} + Er^{10} + Fr^{12} + Gr^{16} + Hr^{18} + Jr^{20}$$

where:

z is the surface sag; c is the curvature at the pole of the surface (CUY); and k is the conic constant (K). A, B, C, D, E, F, G, H, and J are the $4^{th}$, $6^{th}$, $8^{th}$, $10^{th}$, $12^{th}$, $14^{th}$, $16^{th}$, $18^{th}$; and $20^{th}$ order are the deformation coefficients, respectively.

r is the radial distance=$\sqrt{x^2+y^2}$.

For the design of FIG. 6A, the following values may be used for the aspheric constants of the M2, M3, and M4 mirrors as listed in Table 3 below:

TABLE 3

4-Mirror Embodiment Aspheric Constants

| Mirror No. | c | K | A, B, C |
|---|---|---|---|
| 2 | $-2.5030 \times 10^{-2}$ | 0.88479 | $1.0314 \times 10^{-6}$, $-7.3632 \times 10^{-11}$, $5.0828 \times 10^{-13}$ |
| 3 | $-5.0876 \times 10^{-3}$ | $-7.6649$ | $-1.1499 \times 10^{-7}$, $6.5016 \times 10^{-12}$, 0 |
| 4 | $-1.0265 \times 10^{-2}$ | 40.8288 | $5.4572 \times 10^{-6}$, $6.7763 \times 10^{-8}$, 0 |

It is preferable for the diameter of the large mirror to be less than 250 mm in diameter. Larger mirrors will generally take longer to manufacture and take more space and time to coat it. However, extremely small aspherical mirrors are also difficult to make.

As shown, mirrors M1, M3, and M4 have central openings through which reflected light from at least another mirror may pass. For instance, mirror M4 has an opening 610 through which light reflected from mirror M2 (604) passes. Mirror M3 (606) has opening 612 through which light reflected from mirror M4 (608) passes. Mirror M1 has opening 609 through which light reflected from mirror M2 passes.

Each opening may also be placed at an obscured position for light reflected from at least one preceding mirror, the object of interest, or other object. As shown, the second M2 mirror (604) also partially obscures the M1 mirror (602) from the incoming light from the target. In other words, part of the area of the M1 mirror 602 is blocked by the M2 mirror 604 from receiving the light 126 reflected from the target substrate 106. Furthermore, the light reflected by the M2 mirror (604) passes through opening 609 of mirror M1 to reach the M3 mirror (606), which reflects such light towards the M4 mirror (608), which reflects the light towards the sensor 110.

The system of FIGS. 6A and 6B also includes a stop 630 positioned at mirror M1.

The NA specification can be determined by the sensitivity requirements for a particular node. Typically, the higher the NA, the better the system performance. However, the NA can be stopped down to a smaller value. In certain embodiments, the NA for the objective optics is selected to have a range that is 0.3 to 0.99 NA. For this implementation of the objective optics of FIGS. 6A-6B, the NA is to be 0.9, and the magnification is 600×. However, the NA can be larger for alternative embodiments. The magnification specification can depend on the pixel size of the sensor type that is being implemented in the inspection system. In another embodiment with an NA in the 0.3 to 0.95 range, the magnification has a range of 10 to 1500.

The field of view specification is typically selected to achieve relatively short inspection times. In certain implementations, the field of view achieved by the objective is at least 40 microns (μm) in linear size and more specifically at least 600 μm in linear dimension. For instance, the field of view can be between 40 μm and 600 μm. For the embodiment of FIGS. 6A and 6B, the size of the field of view can be 100 microns.

The working distance is the distance between the target substrate 106 and the nearest optical element, typically the mirror M2 604. However, in this case, it is the M1 mirror 602 since this mirror 602 is pushed away from mirror 106 to reduce the central obscuration. A working distance is selected to provide sufficient space for illumination of the target substrate 106 and mounting of the nearest optical element (e.g., M1 mirror 602). In general example, the working distance is at least 10 millimeters (mm). In the illustrated embodiment of FIGS. 6A and 6B, the working distance from the curved surface is much larger than 20 mm so that even after leave room for the reasonable substrate thickness of M1 and its mounting hardware.

The total track may be defined as the distance from the target substrate 106 to the sensor 110. In general, the total track size is limited by available clean room space in which the tool is to be placed. In this particular embodiment, the total track is about 7620 mm, which means folding of the beam path might be necessary. It is desirable to minimize the number of foldings to reduce the impact to the system light budget.

Figure 7A:
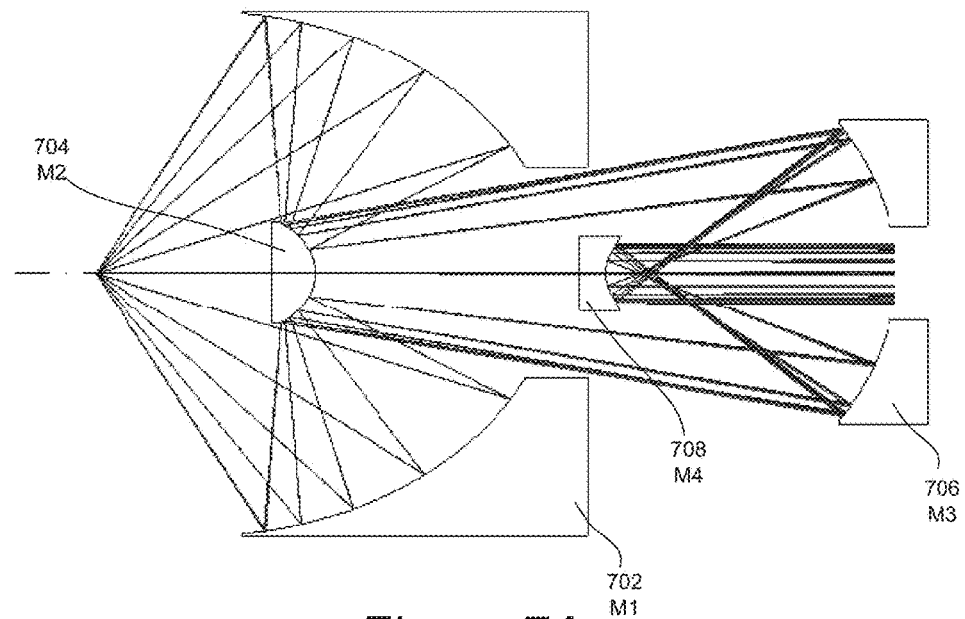
FIGS. 7A and 7B illustrate another 4-mirror design in accordance with a second embodiment of the present invention.
Figure 7B:
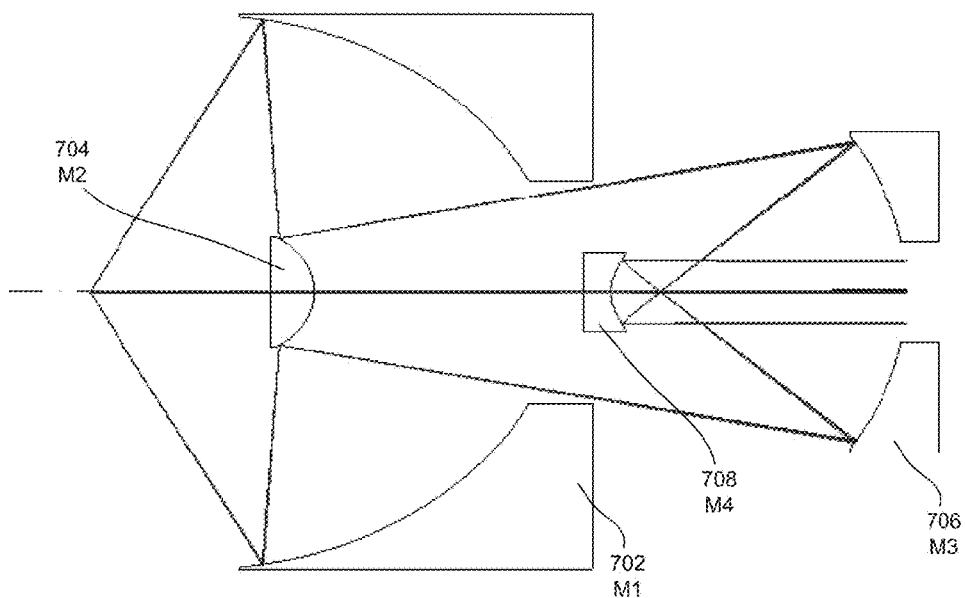

FIGS. 7A and 7B illustrate another 4-mirror design in accordance with a second embodiment of the present invention. From the wafer surface, there is a first concave spherical mirror M1, a convex spherical mirror M2, a concave aspherical mirror M3, and a concave aspherical mirror M4. Instead of having an intermediate image formed between M2 and M3, the intermediate image forms between M3 and M4. Comparing with the design in FIGS. 6A and 6B, the bending of the ray angle on M2 is less severe, making the decenter and tilt sensitivity of M2 to be less sensitive. The FOV can be larger than the one for FIGS. 6A and 6B. M1 and M2 can be spherical mirrors, making the system cheaper to make. The size of M4 generally is controlled to control the central obscuration. The FOV is about 160 um.

The lens data for this 4 mirror design 2 is listed in Tables 4~6 below. M3 and M4 are q-type Aspheres.

TABLE 4

4-Mirror Embodiment 2 Lens Description

Surface Description

| Element No. | Radius Value | Shape | Type | Thickness | Glass |
|---|---|---|---|---|---|
| Object | Flat | | | 142.809 | |
| 1 | −111.963 | CC | SPH. | −74.677 | REFL |
| 2 (Stop) | −26.787 | CX | SPH | 180.415 | REFL |
| 3 | −120.101 | CC | ASP | −90.363 | REFL |
| 4 | 20.209 | CC | ASP | 8370.089 | REFL |
| IMAGE | Flat | | | | |

This $2^{nd}$ alternative 4-mirror embodiment may also have the following characteristics as illustrated in Table 5:

TABLE 5

4-Mirror Embodiment 2 Characteristics

| Field size | 160 μm |
|---|---|
| Object Space NA | 0.9000 |
| Wavelength | 150.00 nm |

In FIGS. 7A and 7B, the following values may be used for the aspheric constants of the M3 and M4 mirrors as listed in Table 6 below. Designers may wish to explicitly control a surface's axial intercept and axial curvature while also being able to represent a conic exactly. The Q-surface type follows Equation 2:

$$z = \frac{cr^2}{1 + \sqrt{1 - kc^2r^2}} + u^4 \sum_{m=0}^{13} a_m Q_m^{con}(u^2)$$

where z is the surface sag, and $$u = \frac{r}{r_{max}},$$

the ratio of the radius over the maximum radius on this surface. For detailed definition of the Q-surface type, please refer to a paper written by Dr. Forbes as published in Optics Express (Opt. Exp. 15, 5218-5226, 2007).

TABLE 6

4-Mirror Embodiment 2 Aspheric Constants

| Mirror No. | C | k | $r_{max}$ | QC4, QC6, QC8, QC10, QC12 |
|---|---|---|---|---|
| 3 | 8.3264E × 10⁻³ | −0.55643 | 59.823 | −3.2615 × 10⁻¹, −7.3074 × 10⁻³, −4.6907 × 10⁻⁵, 2.6673 × 10⁻⁵, 8.0550 × 10⁻⁶ |
| 4 | 4.9482 × 10⁻² | −1.9344 | 12.487 | −2.5412 × 10⁻¹, −1.9978 × 10⁻², −3.8158 × 10⁻⁴, −8.1521 × 10⁻⁵, 3.5345 × 10⁻⁵ |

Figure 8A:
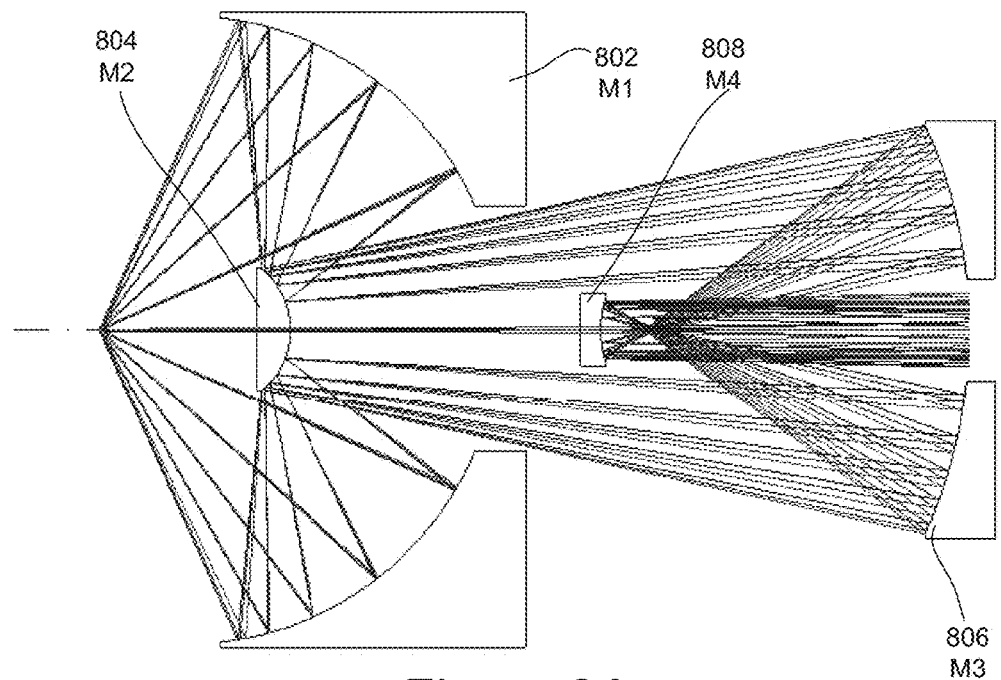
FIGS. 8A and 8B illustrate another 4-mirror design in accordance with a third embodiment of the present invention.
Figure 8B:
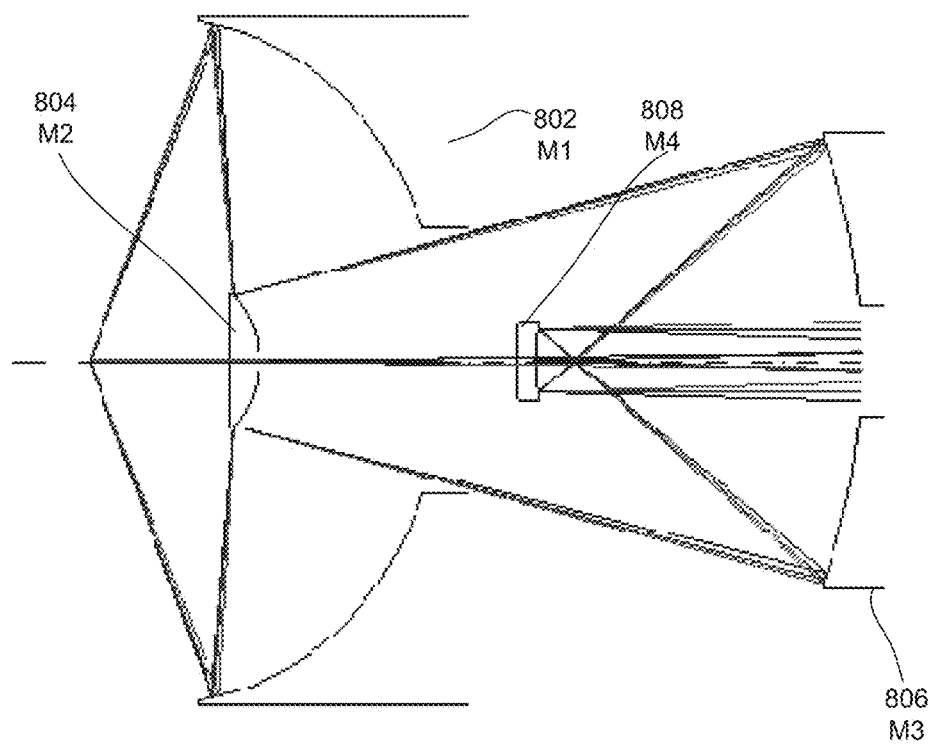

The M1 and M2 mirrors in the design shown in FIGS. 7A and 7B are spherical mirrors, and they can be aspherized to boost the system performance so that a much larger FOV can be achieved. The resulting third design embodiment is illustrated in FIGS. 8A and 8B, and the lens data is listed in Tables 7-9 below. That is, the M1 and M2 mirrors (802 and 804) are aspheric, as well as the M3 and M4 mirrors (806 and 808). In this example, the FOV can be as large as 600 um.

TABLE 7

4-Mirror Embodiment 3 Lens Description

Surface Description

| Element No. | Radius Value | Shape | Type | Thickness | Glass |
|---|---|---|---|---|---|
| Object | Flat | | | 157.323 | |
| 1 | −122.701 | CC | ASP | −82.600 | REFL |
| 2 (Stop) | −31.832 | CX | ASP | 267.167 | REFL |
| 3 | −191.926 | CC | ASP | −144.556 | REFL |
| 4 | 37.768 | CC | ASP | 7415.136 | REFL |
| IMAGE | Flat | | | | |

This alternative 4-mirror embodiment may also have the following characteristics as illustrated in Table 8:

TABLE 8

4-Mirror Embodiment 3 Characteristics

| Field size | 600 μm |
|---|---|
| Objective Space NA | 0.9000 |
| Wavelength | 150.00 nm |

In FIGS. 8A and 8B, the following values may be used for the aspheric constants of the M1, M2, M3, and M4 mirrors as listed in Table 9 below:

TABLE 9

4-Mirror Embodiment 2 Aspheric Constants

| Mirror No. | c | k | $r_{max}$ | QC4, QC6, QC8, QC10, QC12, QC14, QC16 |
|---|---|---|---|---|
| 1 | −8.1499 × 10⁻³ | 0 | 120.52 | −3.6001 × 10⁻¹, 1.9628 × 10⁻², −6.5318 × 10⁻³, −8.0127 × 10⁻⁴, −5.3169 × 10⁻⁴, −6.5254 × 10⁻⁵, −1.8048 × 10⁻⁵ |
| 2 (Stop) | −3.1415 × 10⁻² | 0.42587 | 23.254 | 4.7365 × 10⁻¹, 1.2008 × 10⁻¹, 1.4773 × 10⁻², 4.3797 × 10⁻³, 7.4287 × 10⁻⁴, 2.1459 × 10⁻⁴, 1.2908 × 10⁻⁵ |
| 3 | −5.2103 × 10⁻³ | −0.22289 | 78.445 | 3.0005 × 10⁻², 2.2819 × 10⁻⁴, −1.1941 × 10⁻³, 3.4309 × 10⁻⁴, −7.3096 × 10⁻⁵, 1.614 × 10⁻⁵, −1.1643 × 10⁻⁶ |
| 4 | 2.6478 × 10⁻² | −22.088 | 11.172 | 2.3209 × 10⁻¹, 3.3854 × 10⁻², −1.3200 × 10⁻³, 1.7092 × 10⁻³, 2.6192 × 10⁻⁴, 7.6261 × 10⁻⁵, 6.5515 × 10⁻⁶ |

Figure 9A:
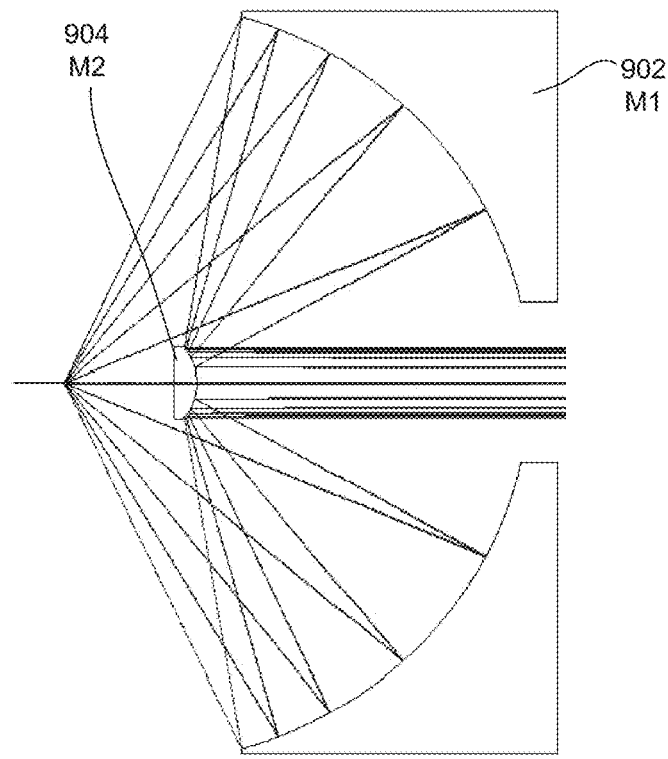
FIGS. 9A and 9B illustrate a diagrammatic representation of a Schwartzchild design in accordance with an alternative implementation of the present invention.
Figure 9B:
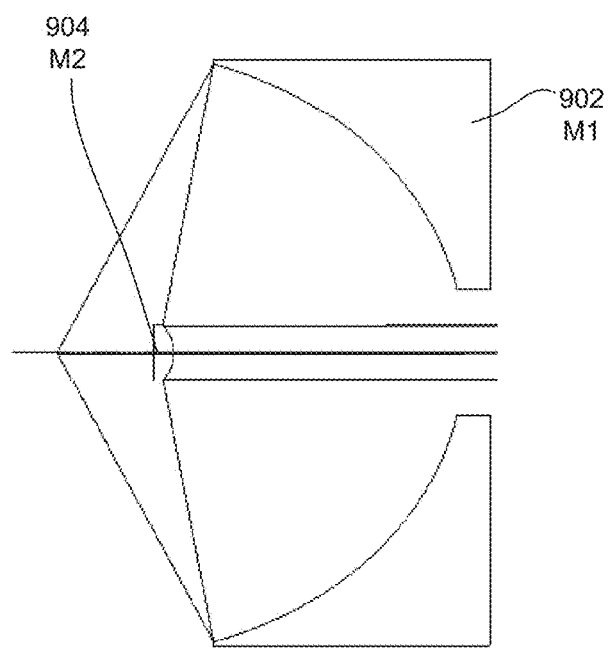

A two mirror Schwartzchild design may also be configured. FIGS. 9A and 9B illustrate a diagrammatic representation of a Schwartzchild design in accordance with one embodiment of the present invention. As shown, this design comprises a concave aspherical mirror M1 (902) and a convex aspherical mirror M2 (904). In order to increase the NA of the system to 0.9, while increasing the FOV, both mirrors are asperized. The central obscuration is limited to a very reasonable 0.22 NA, Comparing with the previous three designs, the FOV is 80 um, slightly smaller. However, the design of FIGS. 9A and 9B utilizes only two mirrors so as to provide a lower cost objective. In this particular design, the size of M2 is 20 mm in diameter, and the size of M1 is about 232 mm.

The lens listing for the design in FIGS. 9A and 9B is listed in Table 10.

TABLE 10

Lens listing for 2M design 1

Surface Description

| Element No. | Radius Value | Shape | Shape Type | Thickness | Glass |
|---|---|---|---|---|---|
| Object | Flat | | | 163.800 | |
| 1 | −143.765 | CC | ASP | −117.000 | REFL |
| 2 (Stop) | −22.223 | CX | ASP | 8510.789 | REFL |
| IMAGE | Flat | | | | |

This alternative 2-mirror embodiment may also have the following characteristics as illustrated in Table 11:

TABLE 11

2-Mirror Embodiment 1 Characteristics

| Field size | 80 μm |
|---|---|
| Object Space NA | 0.9000 |
| Wavelength | 150.00 nm |

In FIGS. 9A and 9B, the following values may be used for the aspheric constants of the M1 and M2 mirrors as listed in Table 12 below:

TABLE 12

2-Mirror Embodiment Aspheric Constants

| Mirror No. | C | k | A, B, C, D, E, F, G |
|---|---|---|---|
| 1 | $-6.9558 \times 10^{-3}$ | 0.008929 | $1.43921 \times 10^{-10}$, $-9.23602 \times 10^{-16}$, $1.84927 \times 10^{-18}$, $-2.16028 \times 10^{-22}$, $1.46346 \times 10^{-26}$, $-5.16453 \times 10^{-31}$, $9.66255 \times 10^{-36}$ |
| 2 (Stop) | $-4.4998 \times 10^{-2}$ | 0.344227 | 0.000000, $-1.05082 \times 10^{-8}$, $2.50151 \times 10^{-10}$, $-4.50642 \times 10^{-12}$, $2.90172 \times 10^{-14}$, $-7.45921 \times 10^{-17}$, 0.000000 |

Figure 10A:
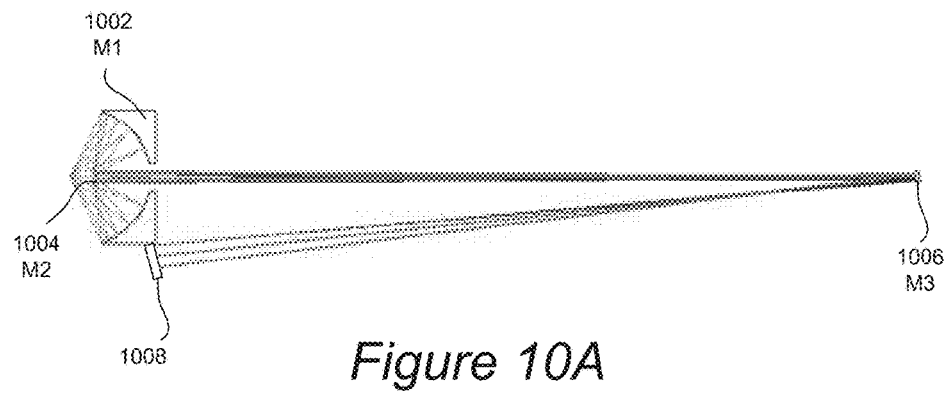
FIGS. 10A and 10B show an alternative embodiment of the two mirror Schwartzchild type design in which a perfect intermediate image is formed and a concave mirror which relays this perfect intermediate image onto the image detector.
Figure 10B:
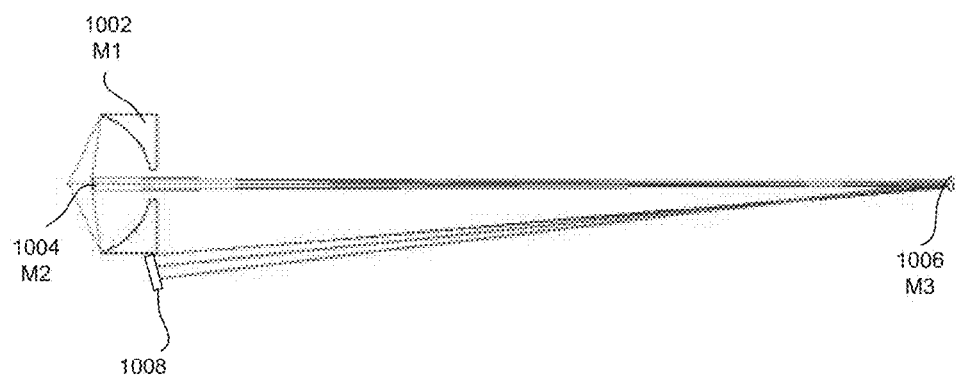

The designs in FIGS. 6A through 9B have relatively long back focal distance. One or more folds of light may be used to limit the system footprint within a reasonable volume. FIGS. 10A and 10B show a variation of the two mirror Schwartzchild type design in which a perfect image, or so called diffraction limited intermediate image, is formed by the two mirror M1 and M2 (1002 and 1004) objective. In this design, a concave mirror M3 (1006) is positioned to relay the perfect intermediate image onto the image detector (1008), which can be a TDI, by way of example, or any other type of sensor.

In more specific embodiments, the magnification range of the first stage, which is from the target to the intermediate image, is between about 2× to 1500×. In other embodiments, this magnification range is between about 10× and 200×. The magnification at the intermediate image can be very large, such as 25× to 50×, or even more, so the NA of the intermediate image is relatively small. For example, for a 50× objective, the NA at the intermediate image will be 0.018 NA. For such a small NA, if the effective focal length of the relay mirror is large compared with the size of the intermediate image, the relay (1006) can be considered as a perfect relay such that no image degradation will be introduced from the intermediate image to the final image sensor (1008). In addition, because of the low NA and relatively small image height compared with the focal length of the relay (1006), the manufacturing tolerance and the integration tolerance will be extremely loose.

The lens description for the design in FIGS. 10A and 10B is listed in Table 13 below. In this design example, the magnification at the intermediate image plane is chosen to be 50×.

As discussed earlier, the size of the last mirror (M2 in the two mirror design and M4 in the four mirror design) is generally minimized to limit the back focal distance, which dominates the overall system footprint. One advantage with the design with the image relay is the alleviation of the requirement to minimize the size of the last mirror before the intermediate image. The size of the small mirror (M2 or M4 correspondingly) can be larger so as to be more manufacturability and reduce the heating load on such mirror.

By varying the distance between the intermediate image and the image relay mirror, different magnification can be achieved, for example, via controller 112. The only drawback is the sensor location will have to be moved for the best focus. In some cases, the sensor, like the TDI sensor, is cumbersome with all the wiring and cabling being connected. One single mirror can serve the purpose of achieving all necessary magnifications. In order to minimize the movement range of the image sensor, multiple relay mirrors with different effective focal length can be utilized. The loose integration tolerance makes it possible to switch in different sets of mirror relays.

This relay is not limited to be a single mirror, it can be replaced with a single or multiple lenses. In some cases, multiple mirrors can be utilized to make the image plane stationary.

The lens listing for the design in FIGS. 10A and 10B is listed in Table 13 below. Element 3 is where the perfect intermediate image locates.

TABLE 13

Lens listing for 2M design with relay

Surface Description

| Element No. | Radius Value | Shape | Type | Thickness | Glass |
|---|---|---|---|---|---|
| Object | Flat | | | 171.278 | |
| 1 | −146.366 | CC | ASP | −118.122 | REFL |
| 2 (Stop) | −19.448 | CX | ASP | 1455.914 | REFL |
| 3 | Flat | | | 289.287 | |
| 4 | −511.301 | | Tilted | −1636.250 | REFL |
| IMAGE | Flat | | | | |

This alternative 2-mirror embodiment with a relay may also have the following characteristics as illustrated in Table 14:

TABLE 14

2-Mirror with Relay Characteristics

| | |
|---|---|
| Field size | 80 μm |
| Object Space NA | 0.9000 |
| Wavelength | 150.00 nm |

In FIGS. 10A and 10B, the following values may be used for the aspheric constants of the M1 and M2 mirrors as listed in Table 15 below:

TABLE 15

Aspheric Constants for 2-Mirror with Relay

| Mirror No. | c | k | A, B, C, D, E, F, G |
|---|---|---|---|
| 1 | $-6.8322 \times 10^{-3}$ | 0.001254 | $1.07366 \times 10^{-10}$, $1.11039 \times 10^{-15}$, $1.17970 \times 10^{-18}$, $-1.63450 \times 10^{-22}$, $1.27486 \times 10^{-26}$, $-5.00128 \times 10^{-31}$, $9.13862 \times 10^{-36}$ |
| 2 (Stop) | $-5.1419 \times 10^{-2}$ | 0.220166 | 0.000000, $8.88067 \times 10^{-10}$, $2.61603 \times 10^{-11}$, $3.20567 \times 10^{-12}$, $2.90172 \times 10^{-14}$, $-7.4826 \times 10^{-17}$, $-2.01052 \times 10^{-19}$ |

In Table 13 above, element 4 corresponds to the M3 mirror (1006), which is tilted about 3 degrees.

Similar to the two mirror Schwartzchild objective, all the four mirror design as in FIGS. 6A through 8B can take advantage the same principle to relay a "perfect" intermediate image onto the image sensor by using a low NA image relay.

Another huge advantage of the system having one or more relay with relatively small NA is the simplicity in the design and implementation of the autofocus and the illumination system design. By choosing the correct NA at the intermediate image, which can be optimized to be a perfect image, by placing the FS (field stop) directly at the conjugate of the intermediate image, all the extra lens and optics between the Field stop and the imaging objective can be eliminated, while a perfect relay from the field stop to the wafer can be achieved automatically. An NA having a range of 0.0006 to 0.45 would work; a preferred range of 0.0045 to 0.09 works well.

Similar to the imaging path, the alignment of the Autofocus and illumination path will be extremely easy because of the low NA at the system interface.

Figure 11A:
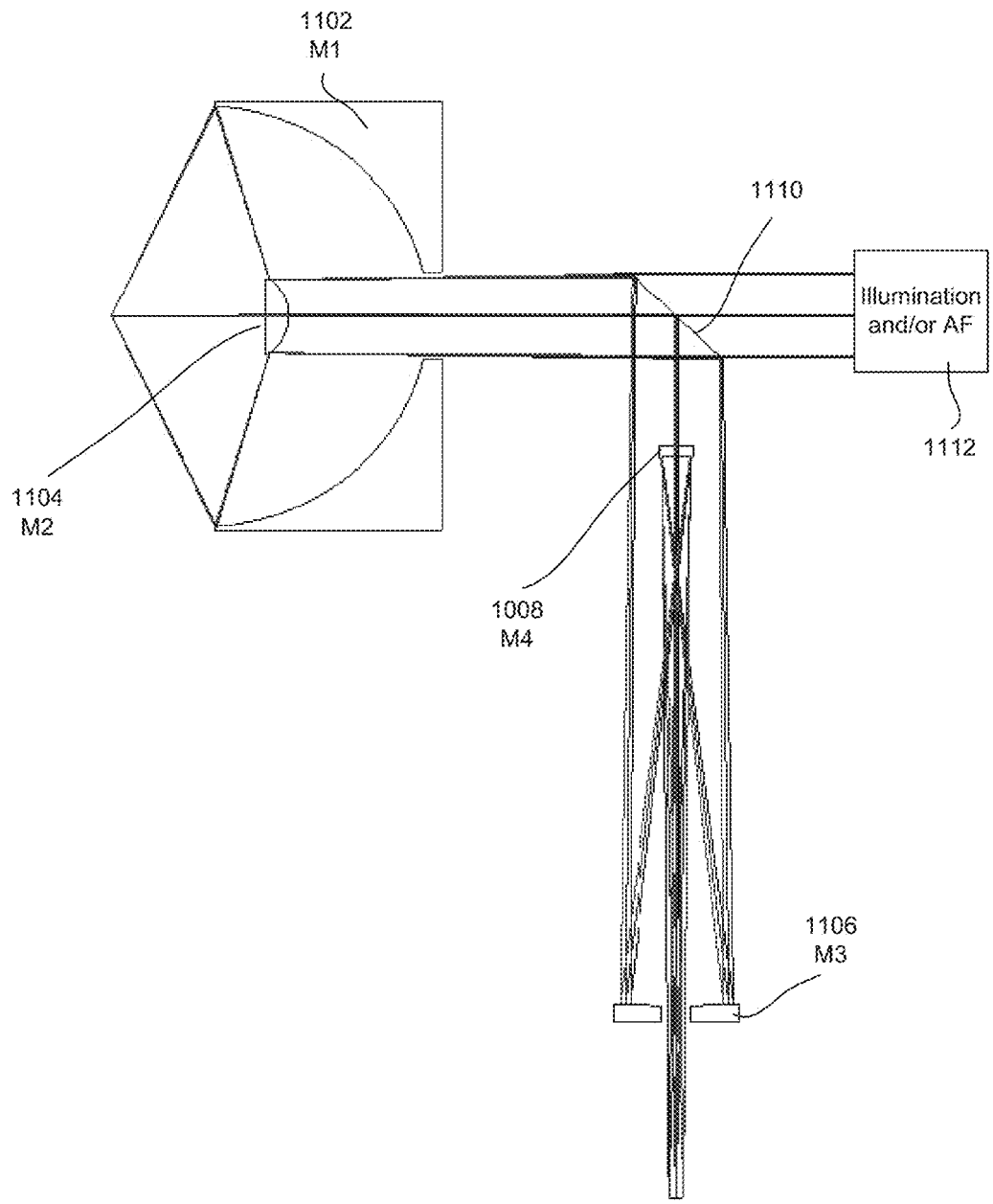
FIGS. 11A and 11B show a 4-mirror design with illumination and/or autofocus insertion in accordance with another embodiment of the present invention
Figure 11B:
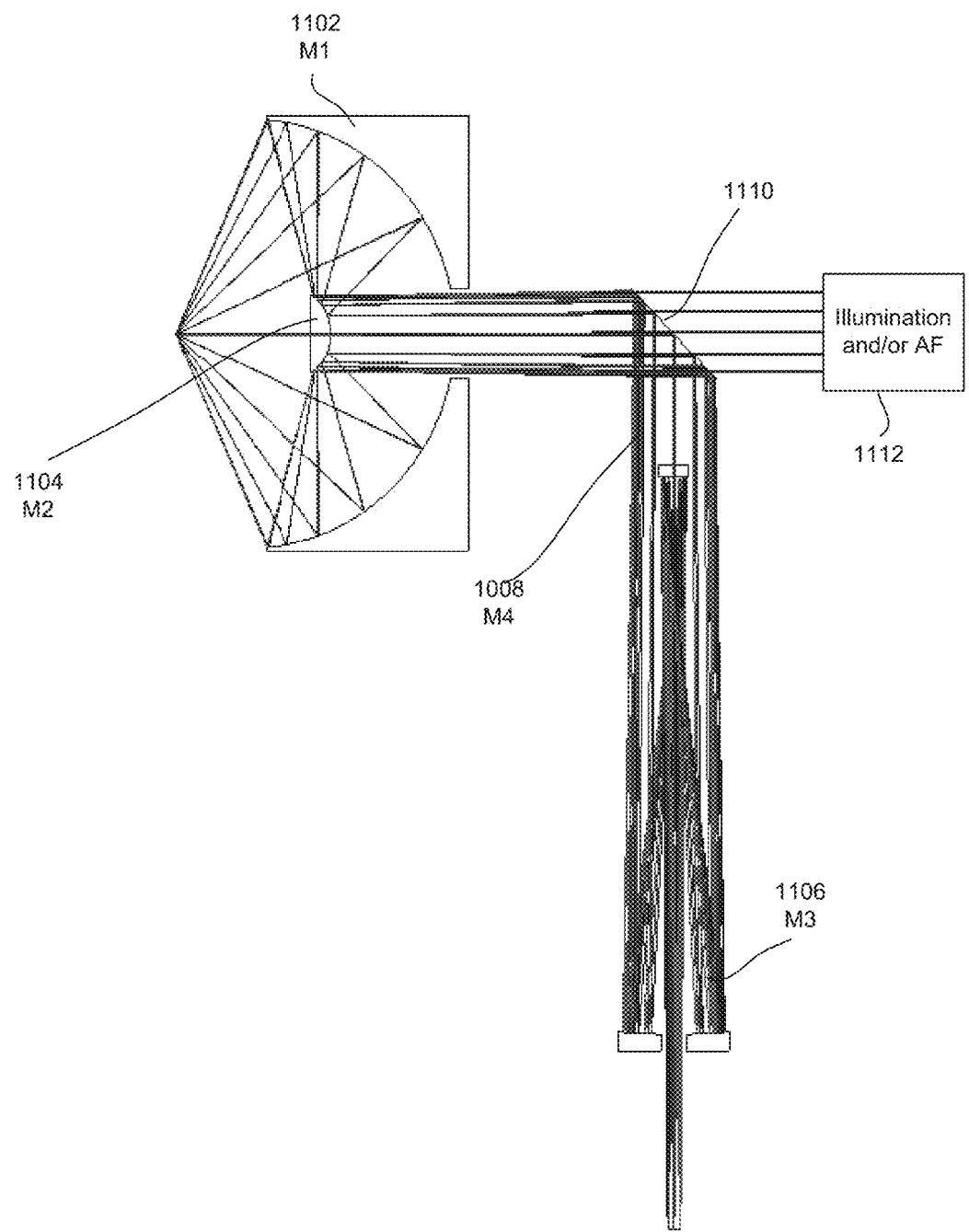

For the four mirror design, the gap of between M2 (e.g., 904) and M4 (e.g., 908) can be increased to allow the insertion of the illumination and/or autofocus into the objective M1/M2 assembly. FIGS. 11A and 11B illustrate such a system that has an increased gap and autofocus insertion point for inserting an illumination and/or autofocus (AF) module (1112) between the M2 mirror (1104) and the M4 mirror (1108) via insertion of a beam splitter (1110) or the like. One example of an illumination module includes a light source (e.g., 102) and optics (e.g., 104) for directing one or more incident beams towards the target 106.

Sometimes it is desirable to make the light between M2 (1104) and M3 (1106) to be close to collimated to reduce the complexity in the illumination path, as shown in FIGS. 11A and 11B. In this design example, the magnification is chosen to be 50×.

The lens description for the FIGS. 11A and 11B embodiment is listed in Tables 16-18.

TABLE 16

Lens listing for 4M design with illumination insertion

| | Surface Description | | | |
|---|---|---|---|---|
| Element No. | Radius Value | Shape | Thickness Type | Glass |
| Object | Flat | | 223.049 | |
| 1 | −183.094 | CC | ASP | −138.677 | REFL |
| 2 (Stop) | −30.402 | CX | ASP | 224.803 | REFL |
| 3 | Flat | | −230.000 | |
| 4 | 219.371 | CC | ASP | 153.893 | REFL |
| 5 | −41.305 | CC | ASP | −675.198 | REFL |
| IMAGE | Flat. | | | |

This alternative 2-mirror embodiment with a relay may also have the following characteristics as illustrated in Table 14:

TABLE 17

Characteristics for 4M design with illumination insertion

| | |
|---|---|
| Field size | 360 μm |
| Object Space NA | 0.9000 |
| Wavelength | 150.00 nm |

In FIGS. 11A and 11B, the following values in Table 18 may be used for the aspheric constants of the 4 mirrors:

TABLE 18

Aspheric Constants for 4M design with illumination insertion

| Mirror No. | c | k | A, B, C, D, E, F, G, H |
|---|---|---|---|
| 1 | $-5.4617 \times 10^{-3}$ | $-0.000964$ | $3.24699 \times 10^{-10}$, $-2.73366 \times 10^{-15}$, $-3.60435 \times 10^{-19}$, $-8.55826 \times 10^{-24}$, $1.86664 \times 10^{-27}$, $-8.17695 \times 10^{-32}$, $1.60077 \times 10^{-36}$, $-1.24940 \times 10^{-41}$ |
| 2 (Stop) | $-3.2893 \times 10^{-2}$ | 0.82146 | $5.08873 \times 10^{-6}$, $-5.37727 \times 10^{-9}$, $-1.26471 \times 10^{-11}$, $4.64338 \times 10^{-14}$, $-1.67230 \times 10^{-17}$, $2.34275 \times 10^{-20}$, $-4.46266 \times 10^{-22}$, $7.59964 \times 10^{-25}$ |
| 4 | $4.5585 \times 10^{-3}$ | 1.30177 | 0.000000, $8.88067 \times 10^{-10}$, $-2.61603 \times 10^{-11}$, $3.20567 \times 10^{-12}$, $2.90172 \times 10^{-14}$, $-7.4826 \times 10^{-16}$, $1.60077 \times 10^{-36}$, $-1.24940 \times 10^{-41}$ |

TABLE 18-continued

Aspheric Constants for 4M design with illumination insertion

| Mirror No. | c | k | A, B, C, D, E, F, G, H |
|---|---|---|---|
| 5 | $-2.4210 \times 10^{-2}$ | $-6.1868$ | 0.000000, $8.88067 \times 10^{-10}$, $-2.61603 \times 10^{-11}$, $3.20567 \times 10^{-12}$, $2.90172 \times 10^{-14}$, $-7.4826 \times 10^{-17}$, $1.60077 \times 10^{-36}$, $-1.24940 \times 10^{-41}$ |

In Table 16 above, element 3 corresponds to the beam splitter (1110), which is tilted at 45 degrees, but this one can be any angle as long as there is no ray interference.

All four of the later optical designs have extremely long working distance and can be easily more than 20 mm, which is much larger than the first-presented 4-mirror design. The manufacturability for the mirror that is close to the wafer plane (Mirror M2) is also greatly enhanced. With a thick substrate, the only current option for cooling the optics is air cooling. In addition, the long working distance can enable introduction of the illumination from the side of M1 or even beneath M1.

Certain embodiments of the present invention may also include the introduction of a low NA intermediate image in the system, and use of a single element relay to relay the intermediate image onto the sensor. An intermediate image can be designed to be diffraction limited, since the NA at the relay is relatively small, and the aberration of the relay can have a minimal contribution to the overall system relay. By adjusting the spacing between the relay mirror and the intermediate image, a continuous zoom relay can be configured. This relay also eliminates the need to minimize the size of the last imaging mirror, making the cooling and manufacturing of the smaller mirror more feasible. Additionally, using a powered folding mirror (e.g., 1006) can make the overall system footprint to be reasonably small.

By introducing the intermediate image, the AF and illumination optics may also be much easier to manufacture and align, due to the lower NA at the intermediate image. Diffraction limited performance can be easily achieved by implementation of this concept.

Expressed as a fraction of pupil area, obscuration fractions less than 20-25% are preferred. Obscuration in 4-mirror designs is often created through the blocking or shadowing of light reflected from the target by the second mirror, or M2 as described above. Minimizing the size of both reflecting surface and peripheral support of M2 will minimize obscuration. The design of structural support for M2 provides for sufficient rigidity, so that environmental disturbances or vibrations do not drive or lead to dynamic perturbations of M2 position and, thus, to degradation of image quality through blurring.

Since mirrors for Infrared to VUV light are coated with single or multilayers to reach adequate reflectivity, the range of incidence angles on any of the highly curved elements is also considered, and restricted within the limits of single or multilayer deposition process technology.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the objective system embodiments described above can be utilized in any suitable system for imaging Infrared to VUV light from any object, besides wafers, such as reticles, etc. Accordingly, the present embodiments are to be considered as illustrative and not restrictive, and the invention is not to be limited to the details given herein.

What is claimed is:

1. An apparatus for reflecting, towards a sensor, an illuminating light that is reflected from a target substrate, the apparatus comprising:
    an illumination source for generating Infrared to Vacuum UV spectral band light that illuminates a target substrate;
    objective optics for receiving and reflecting Infrared to Vacuum UV spectral light that is reflected from the target substrate in response to the generated Infrared to Vacuum UV spectral band light that illuminates the target substrate; and
    a sensor for detecting Infrared to Vacuum UV spectral light that is reflected by the objective optics,
    wherein the objective optics comprises
    a first mirror arranged to receive and reflect Infrared to Vacuum UV spectral light that is reflected from the target substrate,
    a second mirror arranged to receive and reflect Infrared to Vacuum UV spectral light that is reflected by the first mirror, wherein the first and second mirrors are arranged and shaped so as to reflect Infrared to Vacuum UV spectral light from the target substrate towards an optical axis of the apparatus, wherein the numerical aperture (NA) for the reflected Infrared to Vacuum UV spectral light received at the second mirror is larger than the NA for the reflected Infrared to Vacuum UV spectral light received at the first mirror so as to result in a working distance for the objective optics greater than 10 mm,
    a third mirror arranged to receive and reflect Infrared to Vacuum UV spectral light that is reflected by the second mirror, wherein the first and second mirrors are arranged to form an intermediate image between the second and third mirror, and
    a fourth mirror arranged to receive and reflect Infrared to Vacuum UV spectral light that is reflected by the third mirror towards the sensor.

2. The apparatus of claim 1, wherein the target substrate is a semiconductor wafer.

3. The apparatus of claim 1, wherein at least one of the first and second mirrors is aspheric so as to reduce a central obscuration on the fourth mirror.

4. The apparatus of claim 1, wherein the first mirror is spherical and the second, third and fourth mirrors are aspheric.

5. The apparatus of claim 4, wherein the first and third mirrors are concave, and the second and fourth mirrors are convex.

6. The apparatus of claim 1, wherein the first and second mirrors are spherical and the third and fourth mirrors are aspheric, and wherein the first, third, and fourth mirrors are concave, and the second mirror is convex.

7. The apparatus of claim 1, wherein the first, second, third, and fourth mirrors are aspheric, and wherein the first, third, and fourth mirrors are concave, and the second mirror is convex.

8. The apparatus of claim 1, wherein a magnification between from the target substrate to an image sensor is between 2× and 1500×.

9. The apparatus of claim 1, wherein a magnification between from the target substrate to the intermediate image is between 2× and 1500×.

10. The apparatus of claim 1, wherein the fourth mirror's size is minimized to limit a back focal distance.

11. The apparatus of claim 1, further comprising one or more folding mirrors to receive light reflected from the fourth mirror and to relay an intermediate image onto the sensor so as to minimize the footprint of the apparatus.

12. The apparatus of claim 11, wherein the one or more folding mirrors comprise a relay mirror, and wherein the apparatus further comprises a positioning mechanisms for moving the relay mirror so as to vary a distance between an intermediate image and the relay and change a magnification.

13. The apparatus of claim 11, wherein the one or more folding mirrors comprise multiple relay mirrors with different focal lengths, and wherein the apparatus further comprises a positioning mechanisms for switching in different ones of the relay mirrors so as to vary a distance between an intermediate image and the relay and change a magnification.

14. The apparatus of claim 1, wherein a gap between the second mirror and the fourth mirror has a size into which illumination and/or autofocus is inserted.

15. The apparatus of claim 14, wherein Infrared to VUV light between the second and third mirrors is near collimated.

16. An objective optics system for reflecting Infrared to vacuum ultra-violet (VUV) spectral band light that is reflected from a target substrate in response to Infrared to VUV light that illuminates the target substrate, the system comprises:
 a first mirror arranged to receive and reflect Infrared to VUV light that is reflected from the target substrate,
 a second mirror arranged to receive and reflect VUV light that is reflected by the first mirror, wherein the first and second mirrors are arranged and shaped so as to reflect Infrared to VUV light from the target substrate towards an optical axis of the apparatus, wherein the numerical aperture (NA) for the reflected Infrared to Vacuum UV spectral light received at the second mirror is larger than the NA for the reflected Infrared to Vacuum UV spectral light received at the first mirror so as to result in a working distance for the objective optics greater than 10 mm,
 a third mirror arranged to receive and reflect Infrared to VUV light that is reflected by the second mirror, wherein the first and second mirrors are arranged to form an intermediate image between the second and third mirror, and
 a fourth mirror arranged to receive and reflect the Infrared to VUV light that is reflected by the third mirror towards the sensor.

17. An apparatus for reflecting, towards a sensor, Infrared to vacuum ultra-violet (VUV) light that is reflected from a target substrate, the apparatus comprising:
 an illumination source for generating Infrared to VUV light that illuminates a target substrate;
 objective optics for receiving and reflecting Infrared to VUV light that is reflected from the target substrate in response to the generated Infrared to VUV spectral band light that illuminates the target substrate; and
 a sensor for detecting Infrared to VUV light that is reflected by the objective optics,
 wherein the objective optics comprises
  a first mirror arranged to receive and reflect Infrared to VUV light that is reflected from the target substrate, and
  a second mirror arranged to receive and reflect Infrared to VUV light that is reflected by the first mirror towards the sensor, wherein the first and second mirrors are arranged and shaped so as to reflect Infrared to VUV light from the target substrate towards an optical axis of the apparatus, wherein the ray numerical aperture (NA) increases on the second mirror as compared to on the first mirror so as to result in a working distance for the objective optics that is greater than 10 mm.

18. The apparatus of claim 17, wherein the first mirror is a concave spherical mirror and the second mirror is a convex spherical mirror, and wherein the first and second mirrors are aspheric.

19. The apparatus of claim 17, wherein a magnification between from the target substrate to an image sensor is between 2× and 1500×.

20. The apparatus of claim 17, wherein a magnification between from the target substrate to an intermediate image is between 2× and 1500×.

21. The apparatus of claim 20, further comprising one or more folding mirrors to receive Infrared to VUV light reflected from the second mirror and relay an intermediate image onto the sensor so as to minimize a size of the apparatus.

22. The apparatus of claim 17, wherein the second mirror's size is minimized to limit a back focal distance.

* * * * *